(12) United States Patent
Palmas et al.

(10) Patent No.: US 8,007,728 B2
(45) Date of Patent: Aug. 30, 2011

(54) SYSTEM, APPARATUS, AND PROCESS FOR CRACKING A HYDROCARBON FEED

(75) Inventors: Paolo Palmas, Des Plaines, IL (US); Robert Mehlberg, Des Plaines, IL (US); Keith Allen Couch, Des Plaines, IL (US); Paul Nishimura, Des Plaines, IL (US)

(73) Assignee: UOP LLC, Des Plaines, IL (US)

( * ) Notice: Subject to any disclaimer, the term of this patent is extended or adjusted under 35 U.S.C. 154(b) by 189 days.

(21) Appl. No.: 12/332,961

(22) Filed: Dec. 11, 2008

(65) Prior Publication Data

US 2010/0152515 A1     Jun. 17, 2010

(51) Int. Cl.
*B01J 8/24* (2006.01)
*B01J 19/26* (2006.01)

(52) U.S. Cl. ......... 422/139; 422/142; 422/144; 422/145

(58) Field of Classification Search ............... 422/139, 422/142, 144, 145
See application file for complete search history.

(56) References Cited

U.S. PATENT DOCUMENTS

| | | | |
|---|---|---|---|
| 3,470,084 A | 9/1969 | Scott | |
| 4,090,948 A | 5/1978 | Schwarzenbek | |
| 4,097,243 A * | 6/1978 | Bartholic | 422/140 |
| 4,787,967 A * | 11/1988 | Herbst et al. | 208/77 |
| 4,871,446 A | 10/1989 | Herbst et al. | |
| 4,961,907 A | 10/1990 | Herbst et al. | |
| 5,154,818 A | 10/1992 | Harandi et al. | |
| 5,451,313 A | 9/1995 | Wegerer et al. | |
| 5,843,377 A | 12/1998 | Fandel et al. | |
| 6,538,169 B1 | 3/2003 | Pittman et al. | |
| 6,558,530 B2 | 5/2003 | Schlosser et al. | |
| 7,247,233 B1 | 7/2007 | Hedrick et al. | |
| 7,312,370 B2 | 12/2007 | Pittman et al. | |
| 2007/0122316 A1 | 5/2007 | Lomas et al. | |
| 2007/0205139 A1 | 9/2007 | Kulprathipanja et al. | |
| 2007/0213573 A1 | 9/2007 | Ross et al. | |

FOREIGN PATENT DOCUMENTS

WO   WO 2007/094770 A1   8/2007

OTHER PUBLICATIONS

Backhurst et al., Process Plant Design, American Elsevier Publishing Company, Inc., 1973, pp. 287-289.

* cited by examiner

*Primary Examiner* — Jennifer A Leung
(74) *Attorney, Agent, or Firm* — James C Paschall

(57) ABSTRACT

One exemplary embodiment can be a fluid catalytic cracking system. The fluid catalytic cracking system can include a reaction zone including a riser having a top and a bottom adapted to receive spent catalyst at a first elevation and regenerated catalyst at a second elevation. Typically, the first elevation is lower than the second elevation. Additionally, the fluid catalytic cracking system can include a gas distributor contained near the bottom of the riser in communication with a hydrocarbon feed.

1 Claim, 3 Drawing Sheets

SYSTEM, APPARATUS, AND PROCESS FOR CRACKING A HYDROCARBON FEED

FIELD OF THE INVENTION

This invention generally relates to a system, an apparatus, and a process for cracking, desirably catalytically, a hydrocarbon feed.

DESCRIPTION OF THE RELATED ART

Processes for cracking hydrocarbon feedstocks can include fluid catalytic cracking (may be abbreviated hereinafter as "FCC"). In such processes, hydrocarbon feedstocks are often contacted with hot, finely-divided catalytic particles. Such FCC processes can utilize a fluidized bed reactor or an elongated transfer line reactor. Exemplary elongated transfer line reactors can include a riser terminating in a reaction vessel.

Generally, various hydrocarbon feedstocks can be subjected to catalytic cracking operations, including light fractions, e.g., a liquid petroleum gas (hereinafter may be abbreviated "LPG") or a heavy fraction such as a vacuum gas oil (hereinafter may be abbreviated "VGO"). Typically, the hydrocarbon feedstock is maintained at an elevated temperature in a fluidized condition for a time sufficient to effect cracking of the feedstock to lower molecular weight hydrocarbons. In many FCC processes, the preferred products can include high octane liquid fuels, such as gasoline, and light olefins, such as ethylene and/or propylene. Such light olefins can be used as a feed to a polymerization unit for making, e.g., plastics, such as polyethylene or polypropylene.

Often, a two-feed system can be used to produce propylene. In such systems, a riser reactor can produce a product including gasoline that can be sent to a separation system. In the separation system, various fractions can be produced. Optionally, a light fraction can be recycled for producing light olefins. Typically, regenerated catalyst can be provided at the base of the riser.

Unfortunately, such designs may have several disadvantages. The presence of the regenerated catalyst at the base of the riser can increase the temperature at that location. Increased temperatures can over-crack the light recycled fraction, and hence, increase coking at the base of the riser. Such results are generally undesirable and can reduce the amount of product at the top of the riser. Consequently, it would be desirable to provide a system that can allow the increased production of light products, such as ethylene and propylene.

SUMMARY OF THE INVENTION

One exemplary embodiment can be a fluid catalytic cracking system. The fluid catalytic cracking system can include a reaction zone including a riser having a top and a bottom adapted to receive spent catalyst at a first elevation and regenerated catalyst at a second elevation. Typically, the first elevation is lower than the second elevation. Additionally, the fluid catalytic cracking system can include a gas distributor contained near the bottom of the riser in communication with a hydrocarbon feed.

Another exemplary embodiment can be an apparatus for cracking a hydrocarbon feed. The apparatus may include a reaction zone and a disengagement zone. Generally, the reaction zone includes a riser and a reaction vessel communicating with the riser. The riser can have a top and a bottom. A top of the gas distributor can be below at least a portion of a spent catalyst inlet and a regenerated catalyst inlet. Typically, the regenerated catalyst inlet is above the spent catalyst inlet.

A further exemplary embodiment can be a process for catalytically cracking a hydrocarbon feed. The process can include providing the hydrocarbon feed including an effective amount of one or more C4-C6 olefins for producing at least one light olefin to a riser. Typically, at least about 99%, by mole, of the hydrocarbon feed is a gas.

The embodiments disclosed herein can provide several benefits. As an example, the presence of the spent catalyst at the bottom of the riser can prevent over-cracking of the hydrocarbon feed, which can contain an effective amount of one or more C4-C6 olefins for producing a desired light olefin product, such as ethylene or propylene. Moreover, due to the presence of the spent catalyst having a lower temperature, coke formation and coke calcining may be reduced. In addition, the hydrocarbon feed can be provided as a gas, which can reduce the heat requirements within the riser and prevent mechanical corrosion due to rapid gas expansion.

DEFINITIONS

As used herein, the term "stream" can be a stream including various hydrocarbon molecules, such as straight-chain, branched, or cyclic alkanes, alkenes, alkadienes, and alkynes, and optionally other substances, such as gases, e.g., hydrogen, or impurities, such as heavy metals, and sulfur and nitrogen compounds. The stream can also include aromatic and non-aromatic hydrocarbons. Moreover, the hydrocarbon molecules may be abbreviated C1, C2, C3 . . . Cn where "n" represents the number of carbon atoms in the one or more hydrocarbon molecules.

As used herein, the term "regenerated catalyst" can refer to catalyst particles exposed to regeneration conditions, typically via combustion of coke deposits, to restore at least a portion of their activity.

As used herein, the term "spent catalyst" may refer to catalyst particles at least partially deactivated by catalytic poisons, such as coke deposits, and thus have a reduced cracking activity as compared to fresh catalyst particles.

As used herein, the term "rich" can mean an amount of generally at least about 50%, and preferably about 70%, by mole, of a compound or class of compounds in a stream.

DETAILED DESCRIPTION

Figure 1:
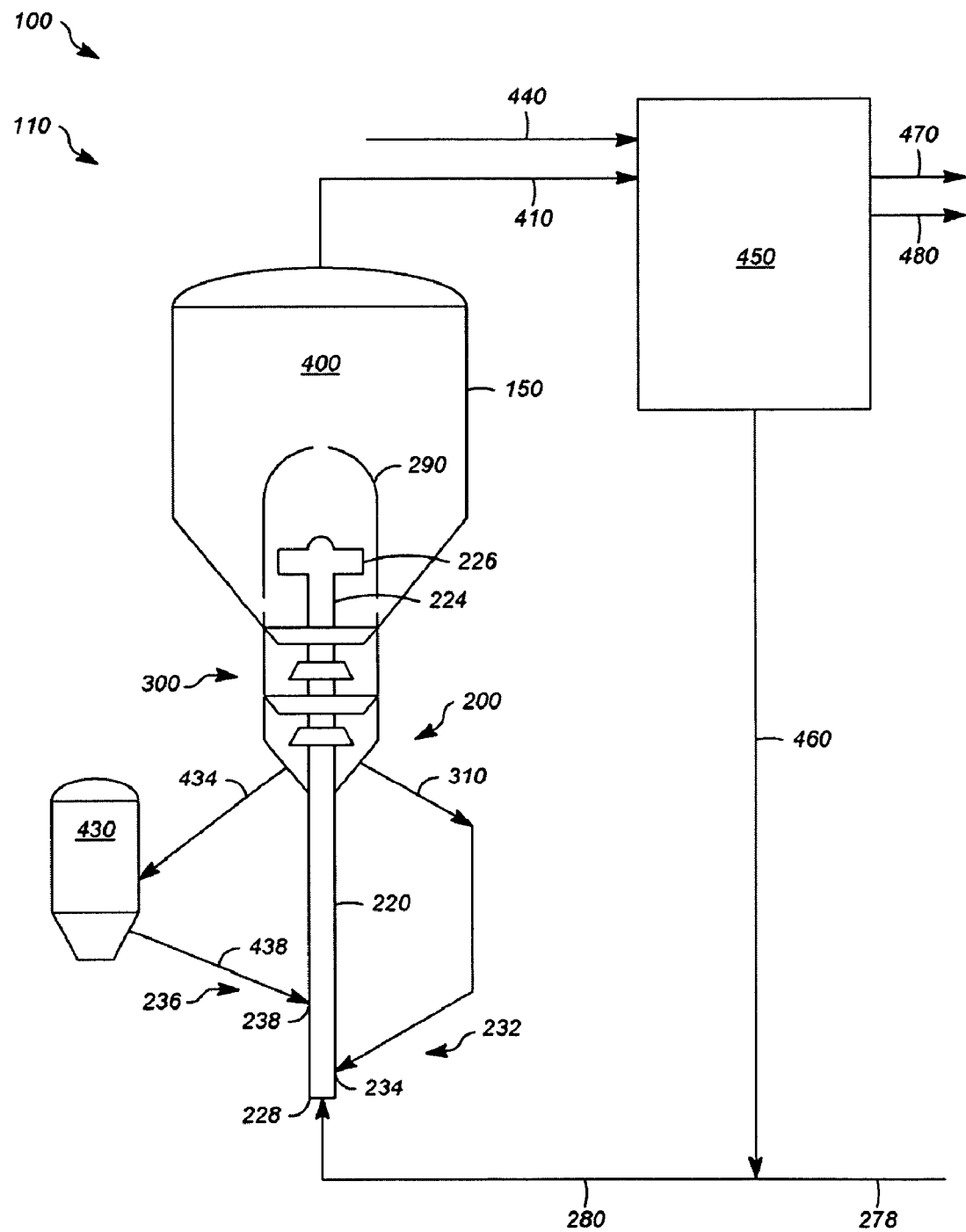
FIG. 1 is a schematic depiction of an exemplary fluid catalytic cracking system.

Referring to FIG. 1, an FCC system 100 can include an apparatus 110, which in turn can include a reaction zone or a first reaction zone 200, a stripping zone 300, a disengagement zone 400, a regeneration zone 430, and a separation zone 450. Exemplary reaction zones, stripping zones, disengagement zones, and regeneration zones, are disclosed in, e.g., U.S. Pat. Nos. 4,090,948; 5,154,818; and 7,312,370 B2. Although a single reaction zone 200 is depicted, it should be understood that other reaction zones may be utilized. Moreover, process flow lines in the figures can be referred to as lines, pipes, conduits, feeds or streams. Particularly, a line, a pipe, or a conduit can contain one or more feeds or streams, and one or more feeds or streams can be contained by a line, a pipe, or a conduit.

Typically, the reaction zone 200 receives a hydrocarbon feed 280 having an effective amount of one or more C4-C6 olefins for producing a light olefin, such as ethylene or propylene, preferably propylene. Generally, the hydrocarbon feed 280 can include about 15-about 75%, about 30-about 50%, by volume, of one or more C4-C6 olefins. In another preferred embodiment, the hydrocarbon feed 280 can include at least about 40%, preferably about 80%, by mole, C4 and/or C6 hydrocarbon, optionally C4 hydrocarbon. In one particular preferred embodiment, the feed 280 can include at least about 40%, preferably at least about 80%, by mole, of butene. Generally, it is desirable for C4 and/or C6 olefins to be present in the hydrocarbon feed 280, although C5 olefins may be present as well.

The hydrocarbon feed 280 can include at least one of a recycle stream 460, as hereinafter described, and a fresh stream 278 supplying the one or more C4-C6 olefins. The fresh stream 278 can supply the requisite hydrocarbons from other units within the refinery or petrochemical manufacturing facility. It should be understood that although two streams 460 and 278 are depicted, any number of additional streams may be utilized. Alternatively, only one stream 460 or 278 may be used.

In addition, it is desirable that the hydrocarbon feed 280 be a gas. The hydrocarbon feed 280 can include at least about 50%, by mole, of the components as a gas. Preferably, the entire hydrocarbon feed 280, i.e., at least about 99%, by mole, is a gas. Generally, the temperature of the hydrocarbon feed 280 can be about 120-about 500° C. Preferably, the temperature of the hydrocarbon feed 280 is no less than about 320° C. Usually, the temperature of the hydrocarbon feed 280 should be at least above the boiling point of the components with an upper limit being that of the catalyst. Generally, it is desirable to have the hydrocarbon feed 280 as a gas from an energy-balanced perspective. Less energy is generally required if the hydrocarbon feed 280 is a gas because gasification of the feed is not required. As a consequence, less catalyst circulation may also be achieved. In addition, a high feed temperature can require less energy to bring the catalyst and hydrocarbon feed 280 up to reaction temperature, and thus further reducing the catalyst recirculation rate. A lower catalyst recirculation rate can reduce the amount of coke produced and yield more valuable products, such as propylene. Moreover, lessening the heat requirements can also reduce coke requirements for producing heat. Hence, heavier feedstocks are not required to produce coke, and greater amounts of feeds with a greater potential to produce lighter products, such as ethylene and propylene, can be utilized. In addition, providing the hydrocarbon feed 280 as a gas minimizes expansion effects of liquid gasification minimizing corrosive effects within the riser 220.

Generally, the FCC system 100 can include at least one reaction zone 200, although other reaction zones may also be provided. Particularly, a separate riser and/or reaction vessel can process a heavy gas oil feed, such as a VGO feed or an atmospheric residue, and produce a high octane product including gasoline. This product can be sent to the separation zone 450 for further processing, as described hereinafter.

Usually, the reaction zone 200 can include a riser 220 terminating in a reaction vessel 290. Generally, the riser 220 has a top 224, a bottom 228, an inlet 234 at a first elevation 232, and an inlet 238 at a second elevation 236. The riser 220 can operate at any suitable temperature, and typically operates at a temperature of about 150-about 430° C. Exemplary risers are disclosed in, e.g., U.S. Pat. Nos. 5,154,818 and 4,090,948.

The riser 220 can receive a mixture of catalyst having pores with openings greater than about 0.7 nanometer (nm) and a second catalyst having smaller openings than the first catalyst. The mixture may be circulated throughout the zones 200, 300, 400, and 430. Such a mixture is disclosed in, e.g., U.S. Pat. No. 7,312,370 B2.

Generally, the first catalyst may include any of the well-known catalysts that are used in the art of FCC, such as an active amorphous clay-type catalyst and/or a high activity, crystalline molecular sieve. Zeolites may be used as molecular sieves in FCC processes. Preferably, the first catalyst component comprises a large pore zeolite, such as a Y-type zeolite, an active alumina material, a binder material, including either silica or alumina, and an inert filler such as kaolin.

The zeolitic molecular sieves appropriate for the first catalyst component should have a large average pore size. Typically, molecular sieves with a large pore size have pores with openings of greater than about 0.7 nm in effective diameter defined by greater than 10 and typically 12 member rings. Pore Size Indices of large pores are above about 31. Suitable large pore zeolite components include synthetic zeolites such as X and Y zeolites, mordent and faujasite. Y zeolites with a rare earth content of no more than about 1.0 weight percent (hereinafter may be abbreviated as "wt. %") rare earth oxide on the zeolite portion of the catalyst may be preferred as the first catalyst.

The second catalyst may include a medium or smaller pore zeolite catalyst exemplified by ZSM-5, ZSM-11, ZSM-12, ZSM-23, ZSM-35, ZSM-38, ZSM-48, and other similar materials. Other suitable medium or smaller pore zeolites include ferrierite, and erionite. The second catalyst preferably has the medium or smaller pore zeolite dispersed on a matrix including a binder material such as silica or alumina and an inert filler material such as kaolin. The second catalyst may also include some other active material such as Beta zeolite. These catalyst compositions can have a crystalline zeolite content of about 10-about 50 wt. % or more and a matrix material content of about 50-about 90 wt. %. Catalysts containing about 40 wt. % crystalline zeolite material are preferred, and those with greater crystalline zeolite content may be used, provided they have satisfactory attrition resistance. Generally, medium and smaller pore zeolites are characterized by having an effective pore opening diameter of less than or equal to about 0.7 nm, rings of 10 or fewer members, and a Pore Size Index of less than 31.

The total mixture may contain about 1-about 25 wt. % of the second catalyst, namely a medium to small pore crystalline zeolite with greater than or equal to about 1.75 wt. % being preferred. When the second catalyst contains about 40 wt. % crystalline zeolite with the balance being a binder material, the mixture can contain about 4-about 40 wt. % of the second catalyst with a preferred content of at least about 7 wt. %. The first catalyst may comprise the balance of the catalyst composition. Usually, the relative proportions of the first and second catalysts in the mixture will not substantially vary throughout the FCC system 100. The high concentration of the medium or smaller pore zeolite as the second catalyst of the catalyst mixture can improve selectivity to light olefins.

Generally, the hydrocarbon feed 280 and the catalyst mixture can be provided to the bottom 228 of the riser 220. The one or more hydrocarbons and catalyst rise to the reaction vessel 290 during which time conversion of the hydrocarbon feed can occur. Typically, a product including propylene is produced. Subsequently, the catalyst can separate assisted by a device, such as swirl arms 226, and settle to the bottom of the reaction vessel 290. In addition, one or more reaction products and entrained catalyst can rise into the disengagement zone 400 contained by a shell 150. Generally, the disengagement zone 400 can include separation devices, such as one or more cyclone separators, for separating out the products from the catalyst particles. Dip legs can drop the catalyst down to the base of the shell 150 where openings can permit the entry of the spent catalyst into the reaction vessel 290. Exemplary separation devices and swirl arms are disclosed in, e.g., U.S. Pat. No. 7,312,370 B2.

The catalyst can pass through the stripping zone 300 where adsorbed hydrocarbons can be removed from the surface of the catalyst by counter-current contact with steam. An exemplary stripping zone is disclosed in, e.g., U.S. Pat. No. 7,312,370 B2.

Catalyst, either regenerated or spent, can be returned to the riser 220 either from the regeneration zone 430 via a conduit 438 or via a conduit 310. At the reaction vessel 290, some catalyst can be withdrawn and sent to a regenerator 430 via a conduit 434. The regenerator 430 can operate at any suitable temperature, such as above 650° C. or other suitable conditions for removing coke accumulated on the catalyst particles. Subsequently, the regenerated catalyst can be returned to the riser via a conduit 438. Any suitable regeneration zone can be utilized, such as those disclosed in, e.g., U.S. Pat. Nos. 4,090,948 and 4,961,907. Generally, the regenerated catalyst has a temperature of about 677-about 760° C. and, more typically, in a range of about 699-about 760° C. The spent catalyst will usually be in a range of about 510-about 621° C.

Generally, the mixture of regenerated and spent catalyst can be provided at two different locations in the riser 220. Particularly, the spent catalyst from the reaction vessel 290 can be provided at the bottom 228 of the riser 220 at a first elevation or point 232 while the regenerated catalyst can be provided at a higher, second elevation or point 238 above the first elevation 232.

The one or more products leaving the disengagement zone 400 can exit through a line 410 to a separation zone 450. Generally, the separation zone 450 can receive the products from the disengagement zone 400 as well as another product stream 440 which can be, e.g., a gasoline product from another fluid catalytic cracking apparatus. Typically, the separation zone 450 can include one or more distillation columns. Such systems are disclosed in, e.g., U.S. Pat. No. 3,470,084. Usually, the separation zone 450 can produce one or more products, such as a stream 470 rich in propylene, a stream 480 rich in a gasoline product, and a stream 460 rich in C4-C6 olefins. Generally, the stream 460 can be recycled to the reaction zone 200 for increasing propylene production.

Figure 2:
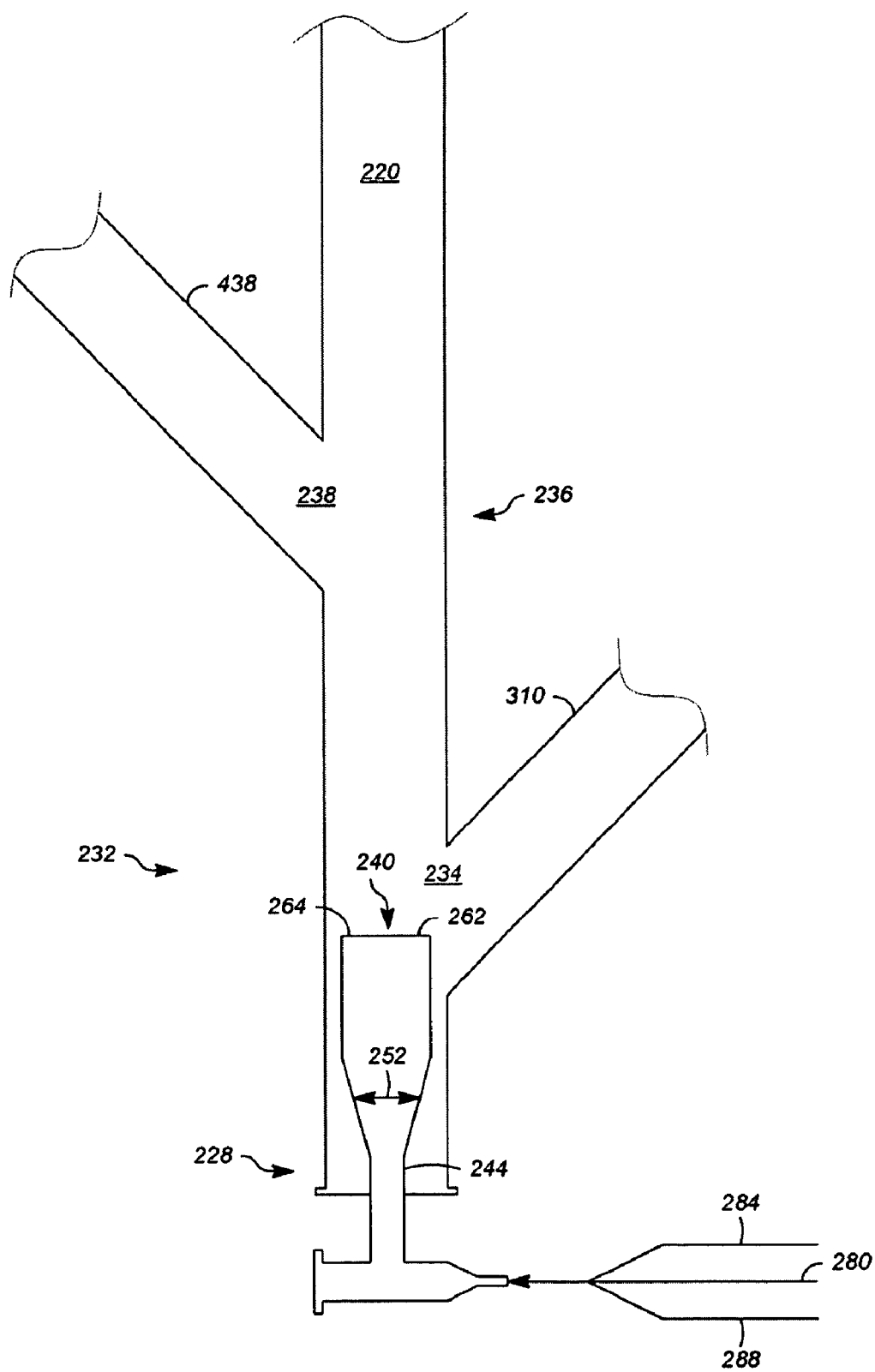
FIG. 2 is a schematic, elevational depiction of an exemplary riser and gas distributor.
Figure 3:
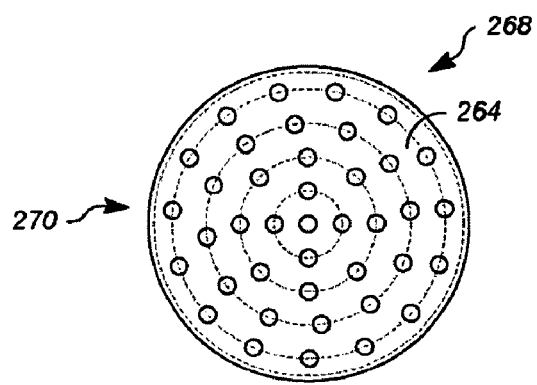
FIG. 3 is a top, plan view of the exemplary gas distributor.
Figure 4:
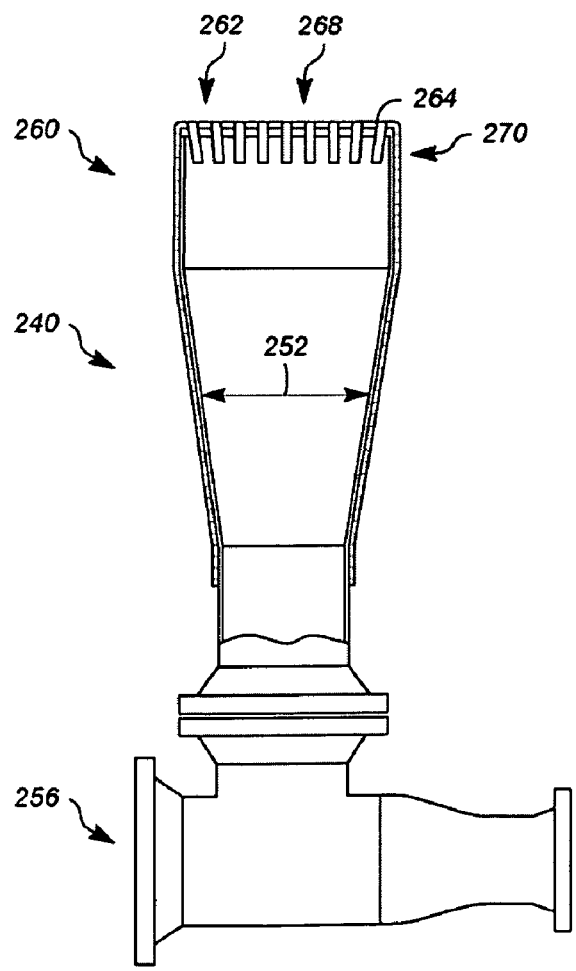
FIG. 4 is a partial cut-away, elevational view of the exemplary gas distributor.

Referring to FIGS. 2-4, a portion of the riser 220 and a gas distributor 240 are depicted. Particularly, the gas distributor 240 can be provided in the bottom 228 of the riser 220. Generally, the gas distributor 240 can receive the hydrocarbon feed 280, which can optionally be combined with steam 284 and a fluidization gas 288. The fluidization gas 288 can be any suitable fluid, such as an inert gas, e.g. nitrogen, or a light hydrocarbon, e.g. methane, ethane, and/or ethylene.

Usually, the gas distributor 240, having a top 260 and a bottom 256, includes a substantially vertically oriented pipe 244 forming an outlet or an opening 262. The substantially vertically oriented pipe 244 has an expanding diameter 252 from bottom to top. This expanding diameter 252 can reduce the rate of fluid flowing upwards through the pipe 244. Generally, the spent catalyst is provided proximate to the outlet 262 of the gas distributor 240. Additionally, the top 260 of the gas distributor 240 can be below at least a portion of a spent catalyst inlet 234 and a regenerated catalyst inlet 238.

Typically, the pipe 244 can have an opening 262 that optionally can be covered with a member or plate 264. Referring to FIG. 3, the member 264 can form a plurality of holes 268 that may be filled with a plurality of tubes 270. Generally, each hole 268 may have a corresponding tube 270. In this exemplary embodiment, the tubes have a uniform diameter, but in other exemplary embodiments, one or more tubes can have a dual diameter, namely an increasing diameter moving from bottom to top. Again, this may help slow the rate of fluid passage through the riser 220.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing, all temperatures are set forth in degrees Celsius and, all parts and percentages are by weight, unless otherwise indicated.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. An apparatus for cracking a hydrocarbon feed, comprising:
   A) a reaction zone, comprising:
      1) a riser having a top and a bottom; wherein the riser comprises:
         a) a gas distributor proximate to the bottom of the riser wherein a top of the gas distributor is below at least a portion of a spent catalyst inlet and a regenerated catalyst inlet wherein the regenerated catalyst inlet is above the spent catalyst inlet, and wherein the gas distributor comprises a pipe having an expanding diameter terminating in an outlet and a member coupled to the pipe proximate to the outlet wherein the member forms a plurality of holes and a plurality of tubes positioned in, respectively, at least some of the plurality of holes but not extending outwardly of said holes;
      2) a reaction vessel communicating with the riser; and
   B) a disengagement zone.

* * * * *